(12) United States Patent
Dell'Oca (10) Patent No.: US 8,968,318 B2
(45) Date of Patent: Mar. 3, 2015

(54) GROOVED CRIMP WITH A SET SCREW

(75) Inventor: Alberto A. Fernandez Dell'Oca, Montevideo (UY)

(73) Assignee: Depuy Synthes Products, LLC, Raynham, MA (US)

(*) Notice: Subject to any disclaimer, the term of this patent is extended or adjusted under 35 U.S.C. 154(b) by 1039 days.

(21) Appl. No.: 12/521,842

(22) PCT Filed: Feb. 28, 2008

(86) PCT No.: PCT/US2008/055226
§ 371 (c)(1),
(2), (4) Date: Jun. 30, 2009

(87) PCT Pub. No.: WO2008/106575
PCT Pub. Date: Sep. 4, 2008

(65) Prior Publication Data
US 2010/0030215 A1 Feb. 4, 2010

Related U.S. Application Data

(60) Provisional application No. 60/903,823, filed on Feb. 28, 2007.

(51) Int. Cl.
*A61B 17/56* (2006.01)
*A61B 17/58* (2006.01)
*A61B 17/82* (2006.01)
*A61F 2/30* (2006.01)
*A61B 17/84* (2006.01)

(52) U.S. Cl.
CPC .............. *A61B 17/82* (2013.01); *A61B 17/842* (2013.01)
USPC .......................................................... 606/74

(58) Field of Classification Search
CPC .. A61B 17/82; A61B 17/842; A61B 17/8861; A61B 17/7053
USPC ........... 606/74, 300, 139, 151, 157, 103, 272, 606/290, 232; 24/135 A, 122.6, 569; 248/63
See application file for complete search history.

(56) References Cited

U.S. PATENT DOCUMENTS 3,239,900 A 3/1966 Bottoms
4,966,600 A 10/1990 Songer et al.
5,190,545 A 3/1993 Corsi et al.
(Continued)

FOREIGN PATENT DOCUMENTS

EP 0019062 11/1980
FR 543126 8/1922
(Continued)

*Primary Examiner* — Kevin T Truong
*Assistant Examiner* — Samuel Hanna
(74) *Attorney, Agent, or Firm* — Fay Kaplun & Marcin, LLP (57) ABSTRACT

A device for binding a cable about a fractured bone to stabilize a fracture comprises a slot including a distal opening sized to receive an enlarged end of a cable and a proximal opening sized to permit the cable to slide therethrough while preventing the enlarged end from passing therethough and a bore sized to slidably receive the cable, the bore extending to a proximal opening in combination with a locking element channel extending to a distal end opening into the bore and a locking element movable into a locking position in which a distal end of the locking element extends into the bore to engage a portion of the cable received therein and lock the cable in a desired position within the bore.

12 Claims, 9 Drawing Sheets

(56) References Cited

U.S. PATENT DOCUMENTS

| | | | |
|---|---|---|---|
| 5,318,566 A | 6/1994 | Miller | |
| 5,324,291 A | 6/1994 | Reis et al. | |
| 5,395,374 A * | 3/1995 | Miller et al. | 606/74 |
| 5,415,658 A * | 5/1995 | Kilpela et al. | 606/300 |
| 5,423,820 A | 6/1995 | Miller et al. | |
| 5,425,767 A * | 6/1995 | Steininger et al. | 623/13.14 |
| 5,449,361 A | 9/1995 | Preissman | |
| 5,536,270 A | 7/1996 | Songer et al. | |
| 5,545,168 A | 8/1996 | Burke | |
| 5,569,253 A | 10/1996 | Farris et al. | |
| 5,607,430 A | 3/1997 | Bailey | |
| 5,649,927 A | 7/1997 | Kilpela et al. | |
| 5,653,711 A * | 8/1997 | Hayano et al. | 606/74 |
| 5,665,088 A | 9/1997 | Gil et al. | |
| 5,665,089 A | 9/1997 | Dall et al. | |
| 5,702,399 A | 12/1997 | Kilpela et al. | |
| 5,741,259 A | 4/1998 | Chan | |
| 5,772,663 A | 6/1998 | Whiteside et al. | |
| 5,797,916 A | 8/1998 | McDowell | |
| 5,810,824 A | 9/1998 | Chan | |
| 5,836,061 A * | 11/1998 | Castillo et al. | 24/702 |
| 5,935,133 A | 8/1999 | Wagner et al. | |
| 5,941,881 A | 8/1999 | Barnes | |
| 5,993,452 A | 11/1999 | Vandewalle | |
| 6,099,527 A | 8/2000 | Hochschuler et al. | |
| 6,387,099 B1 * | 5/2002 | Lange et al. | 606/74 |
| 6,398,787 B1 | 6/2002 | Itoman | |
| 6,576,018 B1 | 6/2003 | Holt | |
| 6,589,246 B1 * | 7/2003 | Hack et al. | 606/74 |
| 6,605,091 B1 | 8/2003 | Iwanski | |
| 6,656,185 B2 * | 12/2003 | Gleason et al. | 606/74 |
| 6,786,932 B1 | 9/2004 | Blackmore | |
| 2002/0091391 A1 | 7/2002 | Cole et al. | |
| 2002/0120282 A1 | 8/2002 | Klipela et al. | |
| 2002/0177852 A1 | 11/2002 | Chervitz et al. | |
| 2003/0014054 A1 | 1/2003 | Huebner | |
| 2003/0083667 A1 * | 5/2003 | Ralph et al. | 606/96 |
| 2004/0087954 A1 | 5/2004 | Allen et al. | |
| 2004/0097942 A1 * | 5/2004 | Allen et al. | 606/72 |
| 2004/0199169 A1 | 10/2004 | Koons et al. | |
| 2004/0225291 A1 | 11/2004 | Schwammberger et al. | |
| 2005/0021033 A1 | 1/2005 | Zeiler et al. | |
| 2005/0043734 A1 | 2/2005 | Kay | |
| 2005/0177179 A1 | 8/2005 | Baynham et al. | |
| 2006/0276896 A1 | 12/2006 | Fallin et al. | |
| 2007/0100345 A1 | 5/2007 | Fernandez | |
| 2007/0265630 A1 | 11/2007 | Marissen et al. | |

FOREIGN PATENT DOCUMENTS

| | | |
|---|---|---|
| FR | 590290 | 6/1925 |
| WO | 94/28812 | 12/1994 |
| WO | 95/03003 | 2/1995 |
| WO | 2006/039900 | 4/2006 |

* cited by examiner

GROOVED CRIMP WITH A SET SCREW

FIELD OF THE INVENTION

The present invention relates generally to orthopedics, in particular, to a crimp used to hold surgical cable after it has been looped around a fractured bone.

BACKGROUND OF THE INVENTION

It is well known to use surgical cable and crimp assemblies to fix parts of a fractured bone and to join them together until the bone heals. Surgical procedures on and in the vicinity of a bone with closely neighboring nerves, arteries, muscle, ligaments, complicated anatomical structures and delicate areas represent a difficult and time consuming task for the surgeon. Thus it is important for the cable and crimp device to be assembled accurately, minimizing stress, trauma, risk, and injury to a patient while facilitating and shortening the procedure.

Furthermore it is desirable to maintain the bulk of the cable as well as the joint where the cable is affixed to itself as compact as possible to minimize discomfort and damage to the surrounding tissue.

Known minimally invasive techniques for such procedures generally involve looping the cable, isolated from the crimp member, about the bone and then inserting a beaded first end of the cable into a cavity of a groove in the crimp member. The groove at the crimp member allows the first end of the cable to slide in place until the bead locks in its final position. The second end of the cable is then inserted through the hole of the crimp member and the cable is tensioned by application of a tensioning tool to the cable through a handle, to a proximal abutment face of the crimp. Once the desired final tension has been established, the set screw is tightened using a screw-driver through the handle, deforming the cable inside the hole. The tensioning tool is then removed and the free end of the cable extending from the proximal abutment face of the crimp is cut off.

Many of the known tools for performing this procedure require pulling the cable from both ends after the cable has been looped around the bone. To access both ends of the cable as required, such devices require significant spreading of the incision and the tissue along the path of the cable increasing trauma to muscle and other surrounding tissue and making them unsuitable for use in restricted areas. Such devices are disclosed, for example, in U.S. Pat. Nos. 5,649,927 and 6,017,347.

Other devices such as that described in allow tensioning of the cable by application of a tensioning tool to one of the cable ends and to an abutment face of the crimp by employing a surgical cable factory crimped to one of the holes of the crimp, as those disclosed in U.S. Pat. Nos. 5,423,820, 6,007,268 and 6,387,099. The same effect is achieved by instruments such as that described in U.S. Pat. No. 6,017,347, that use a wire with a beaded end which locks into an end of the crimp preventing the wire from slipping out of the clamp. The bead locks into the end of the crimp preventing the wire from sliding out of the crimp.

SUMMARY OF THE INVENTION

Accordingly, it is an object of the present invention to provide a compact tool which is easy to assemble and use to secure surgical cable around bone without requiring a large incision and which minimizes the exposure or stripping of musculature away from the bone.

Furthermore, it is an object of the present invention to provide a cable and crimp assembly that enables the cable to be inserted isolated from the crimp member, and the crimp member to be attached to the surgical cable only after the cable has been looped around the bone.

The embodiments of the present invention comprise a flexible cable, a crimp member, a set screw, a handle, and a screw-driver. The surgical cable has an enlargement (e.g., a bead) affixed to its first end and the crimp member has a two-part groove, a cable hole for the cable and an oblique threaded hole for a set screw. The groove has a first part including a cavity sized to accept the beaded end of cable. The second part of groove is sized to allow the flexible cable to pass therethrough while stopping the larger, beaded first end of the cable. The cable hole is sized to accommodate the cable while the oblique threaded hole extends to the cable with an abutment, proximal face of the crimp member located near a proximal end of the cable hole.

The present invention is also directed to a device for binding a cable about a fractured bone to stabilize a fracture comprising a slot including a distal opening sized to receive an enlarged end of a cable and a proximal opening sized to permit the cable to slide therethrough while preventing the enlarged end from passing therethough and a bore sized to slidably receive the cable, the bore extending to a proximal opening in combination with a locking element channel extending to a distal end opening into the bore and a locking element movable into a locking position in which a distal end of the locking element extends into the bore to engage a portion of the cable received therein and lock the cable in a desired position within the bore.

Other objects, advantages and novel features of the present invention will become apparent from the following detailed description of the invention when considered in conjunction with the accompanying drawings.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION

Hereinafter, an apparatus and method for securing surgical cable around a bone according to the preferred embodiment of the present invention will be explained with reference to FIGS. 1-6. As would be understood by those skilled in the art, the term 'proximal' describes a direction approaching a user (e.g., a surgeon) along the item being described while the term 'distal' refers to a direction away from the user along the item being described. Thus, the distal end of a cable refers to an end of the cable furthest from an end extending, for example out of the body to a point accessible to a user, along the cable and not to a portion of the cable located physically furthest from the operator.

As shown in FIGS. 1-4 a binding member 10 according to a first embodiment of the present invention includes an outer surface 12, a bone facing surface 14, a distal end 16 and an abutment surface 18 formed at a proximal end 20 thereof. A groove 22 is formed in the binding member 10 extending distally at an angle from a proximal opening 24 in the abutment surface 18 adjacent to the bone facing surface 14 to a distal end 26. A bore 28 extends from a proximal opening 30 at the distal end 26 of the groove 22 to a distal opening 32 in the distal end 16. The bore 28 is preferably formed as a simple through hole sized to accept a flexible cable 34 to be held by the binding member 10. The groove 22 according to this embodiment is formed as a two-part slotted hole open at the outer surface 12. The proximal opening 24 of the groove 22 is preferably sized so that the cable 34 may slidably pass therethrough while an enlarged first end 36 of the cable 34 is prevented from passing therethrough. The groove 22 may also include a lip 38 (shown in FIG. 2 as the space between the broken lines and the unbroken lines of the groove 22) extending substantially around the perimeter thereof sized to permit the cable 34 to pass slidably therethrough while preventing the enlarged first end 36 from passing through. The rest of the groove 22 (i.e., an interior passage thereof) is preferably sized to permit the cable 34 and the enlarged first end 36 to slide therethrough. In addition, the groove 22 includes an enlarged distal opening 40 at the distal end 26 sized to permit the enlarged first end 36 to be inserted into the groove 22.

Figure 1:
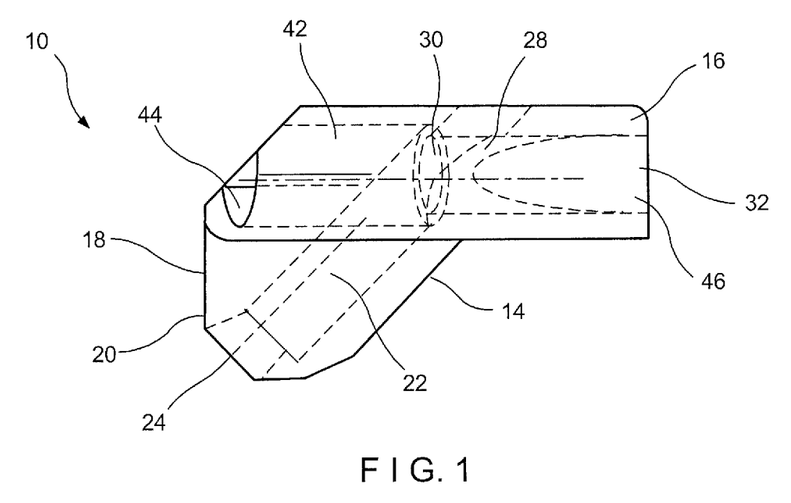
FIG. 1 shows a side view of a crimp device according to the first embodiment of the present invention, prior to assembling with a flexible cable.
Figure 2:
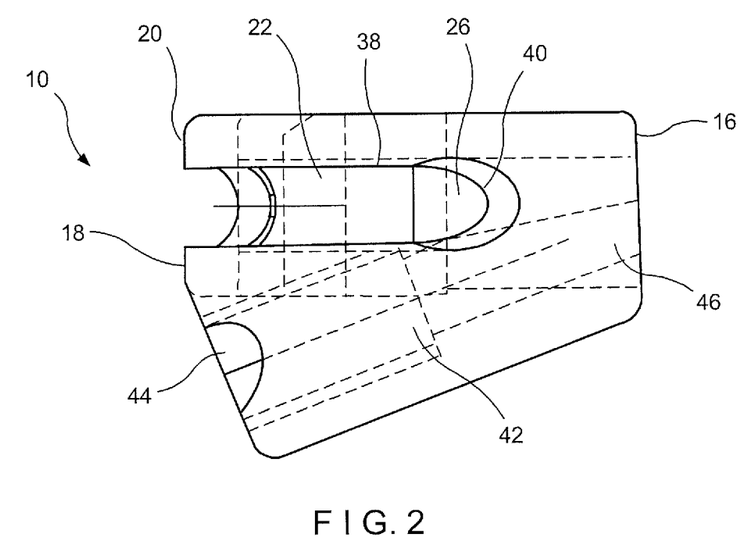
FIG. 2 shows a top view of the crimp device of FIG. 1.
Figure 3:
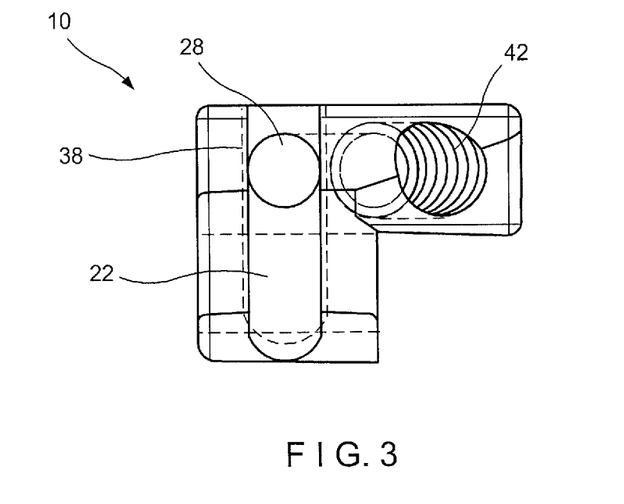
FIG. 3 shows a proximal view of the crimp device of FIG. 1.
Figure 4:
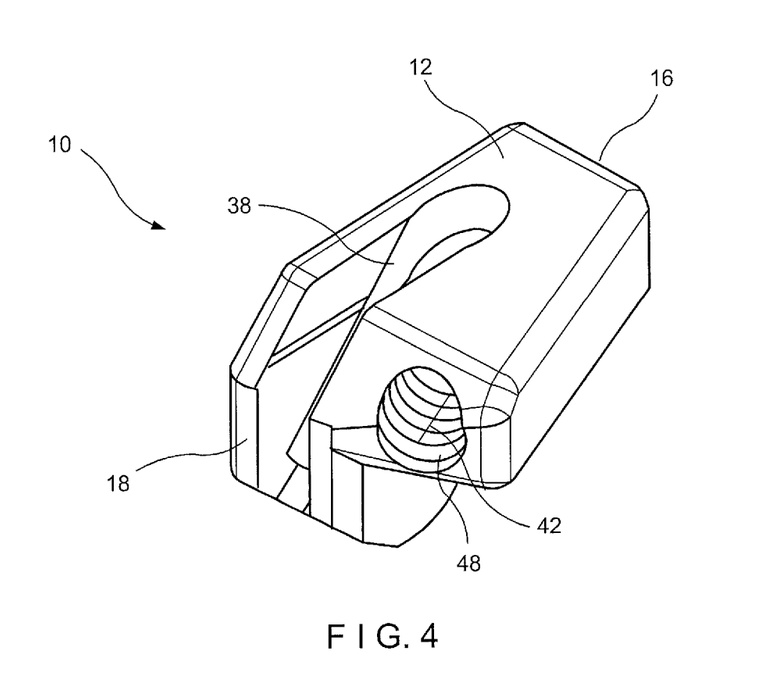
FIG. 4 shows a perspective view of the crimp device of FIG. 1.
Figure 5:
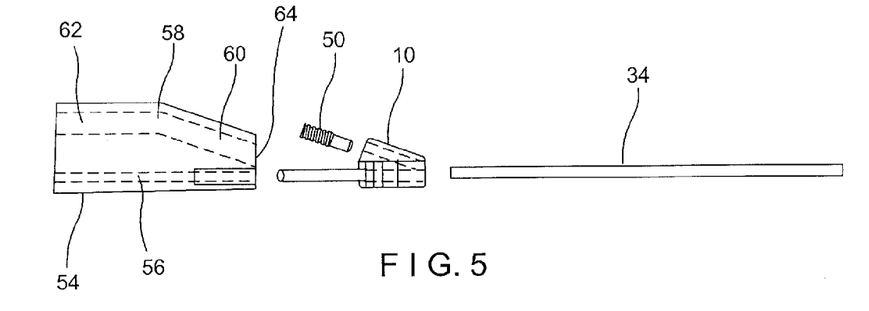
FIG. 5 shows a side view of a disassembled system for fixing a cable about a fractured bone including the crimp device of FIG. 1.
Figure 6:
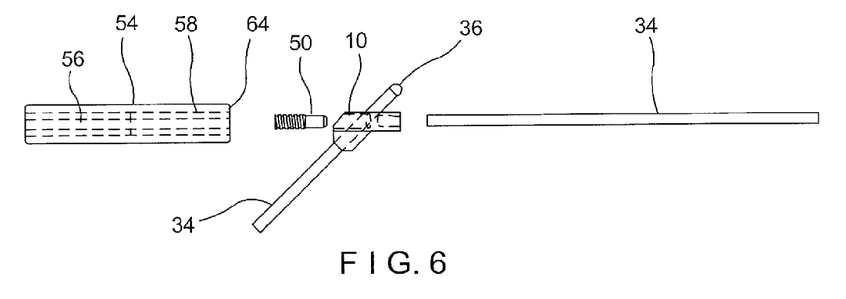
FIG. 6 shows a top view of the system of FIG. 5.
Figure 7:
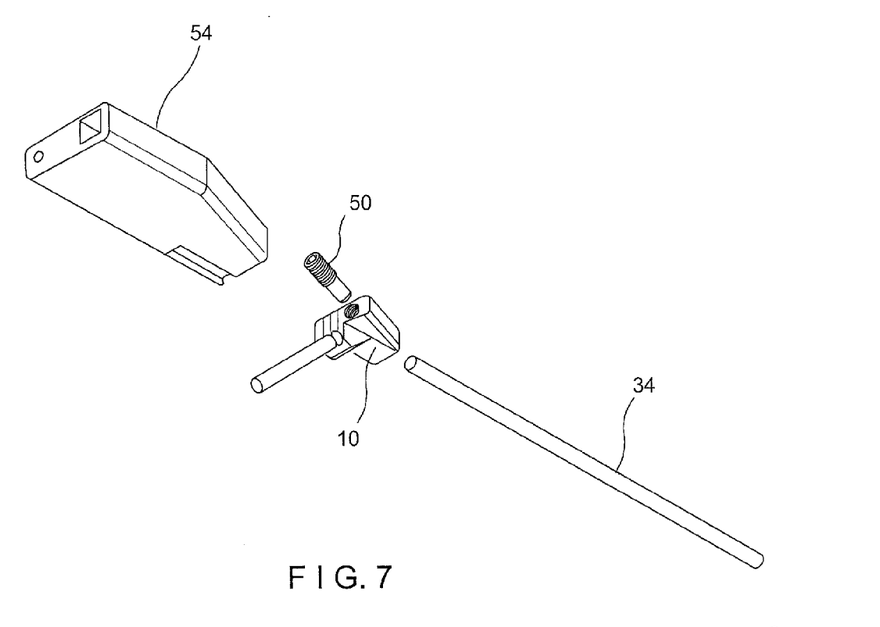
FIG. 7 shows a first perspective view of the system of FIG. 5.
Figure 8:
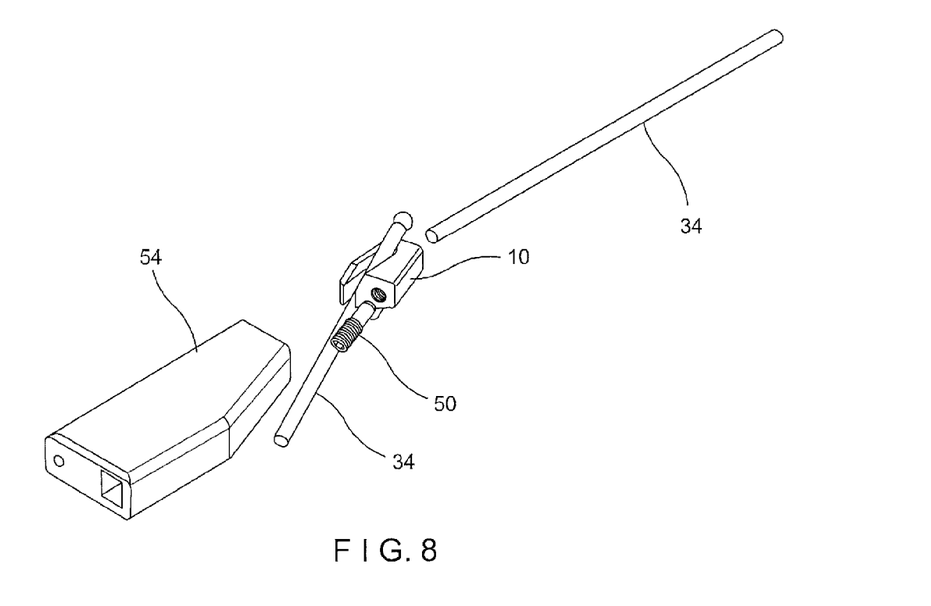
FIG. 8 shows a second perspective view of the system of FIG. 5.
Figure 9:
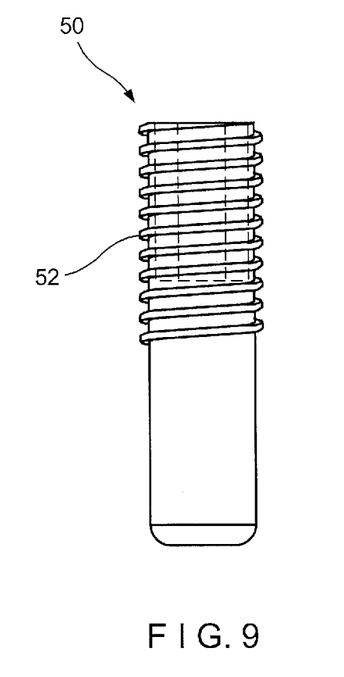
FIG. 9 shows a side view of a set screw for use with a crimp device according to the invention.
Figure 10:
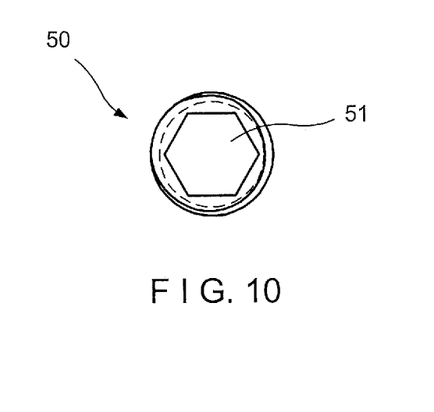
FIG. 10 shows a proximal view of the set screw of FIG. 9.
Figure 11:
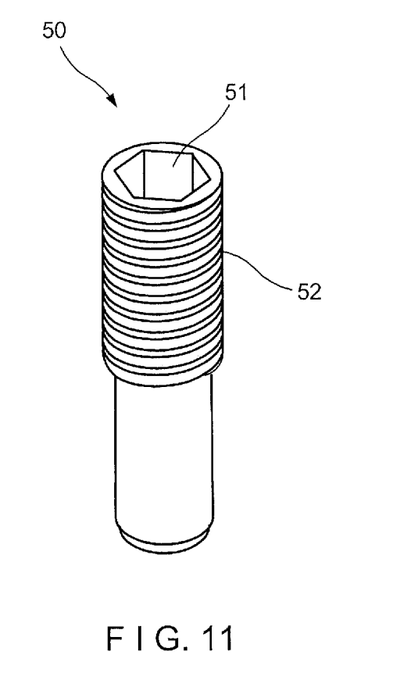
FIG. 11 shows a perspective view of the set screw of FIG. 9.
Figure 12:
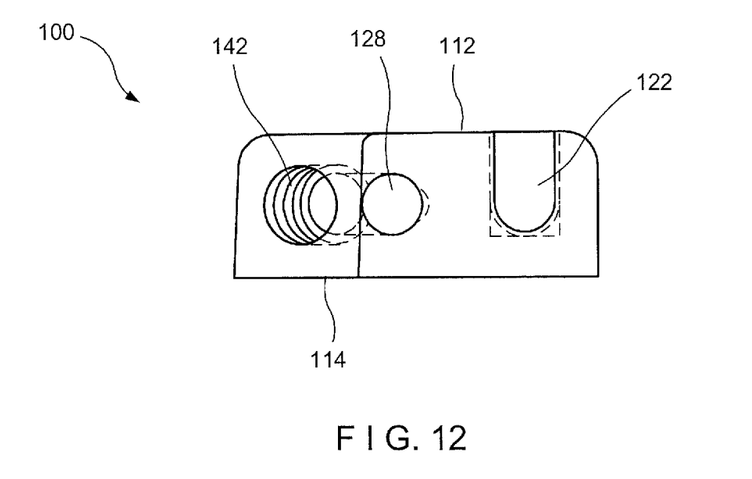
FIG. 12 shows a proximal view of a crimp device according a second embodiment of the present invention, prior to assembling with a flexible cable.
Figure 13:
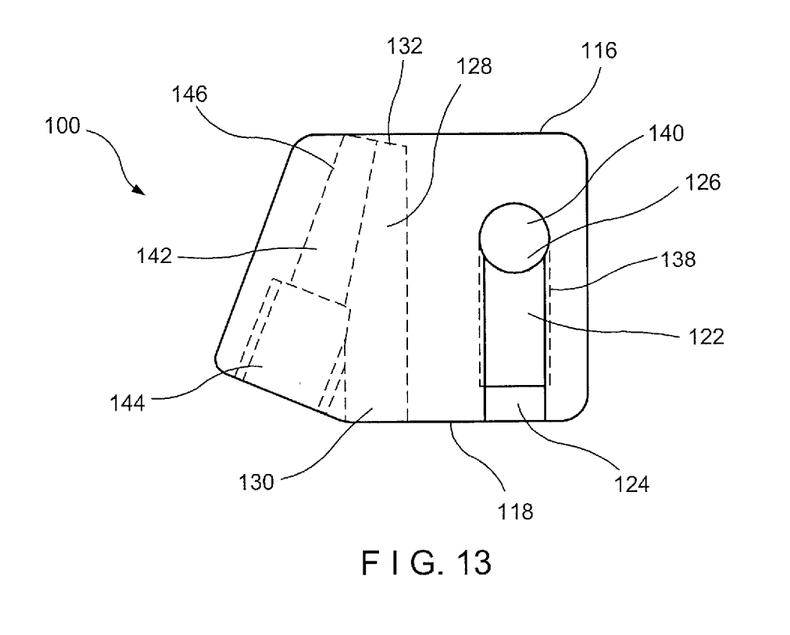
FIG. 13 shows a top view of the crimp device of FIG. 12.
Figure 14:
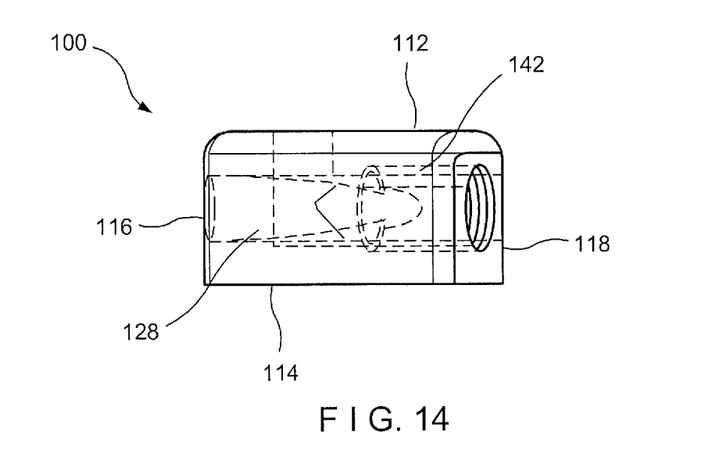
FIG. 14 shows a side view of the crimp device of FIG. 12.
Figure 15:
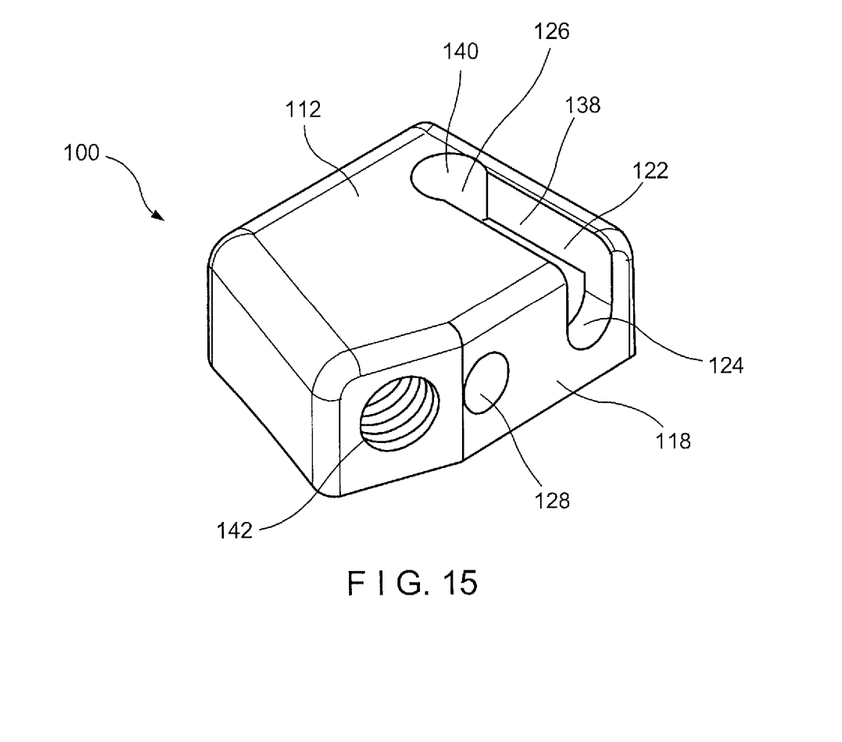
FIG. 15 shows a perspective view of the crimp device of FIG. 12.
Figure 16:
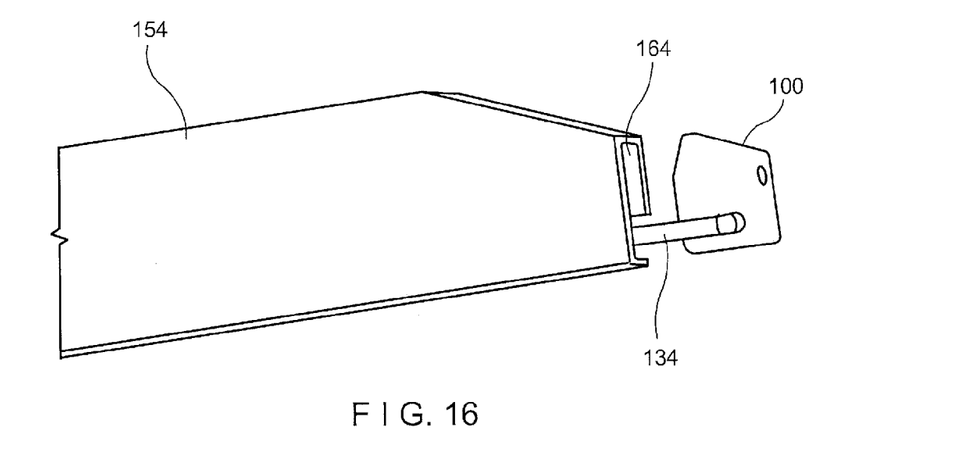
FIG. 16 shows a side view of a system for fixing a cable about a fractured bone including the crimp device of FIG. 12 in a partially assembled state.
Figure 17:
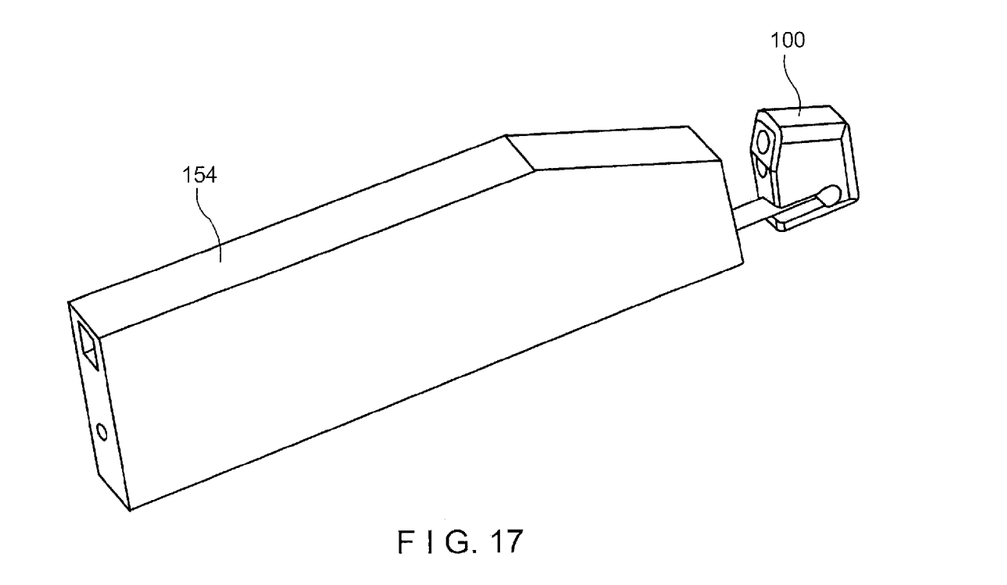
FIG. 17 shows a perspective view of the system of FIG. 16 in a partially assembled state.
Figure 18:
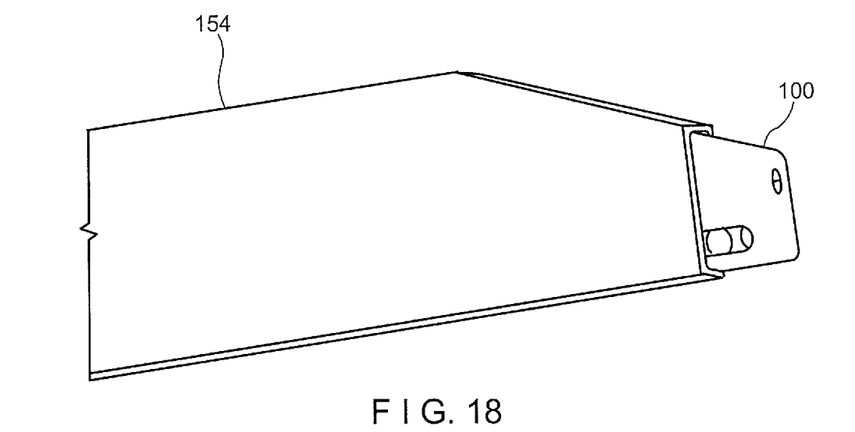
FIG. 18 shows a side view of the system of FIG. 16 in a fully assembled state.
Figure 19:
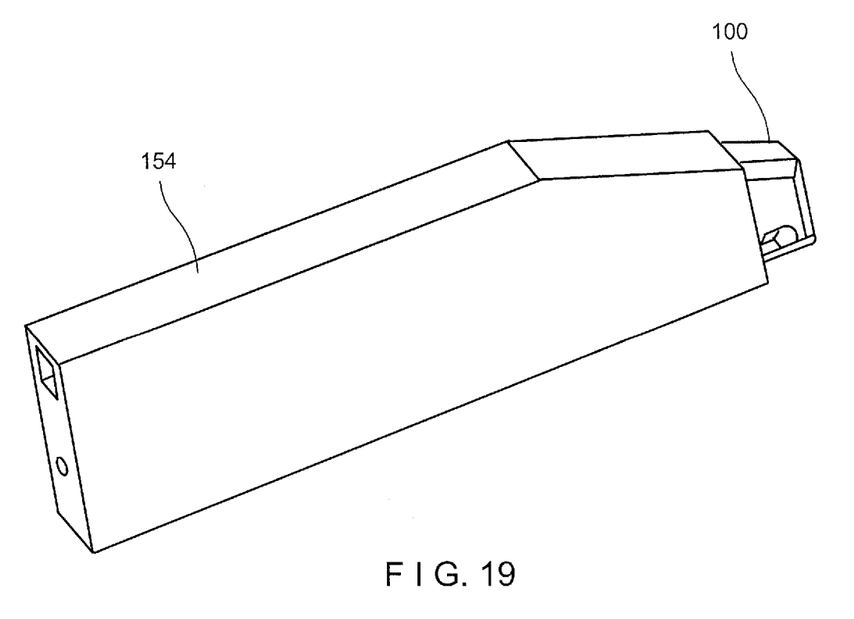
FIG. 19 shows a perspective view of the system of FIG. 16 in a fully assembled state.

The binding member 10 further comprises a locking element channel 42 extending at an angle from a proximal opening 44 to a distal opening 46 into the bore 28. As would be understood by those skilled in the art, although the locking element channel 42 is described in conjunction with the disclosed embodiments as receiving a set screw, any number of alternate locking elements may be employed to lock the cable 34 at a desired position in the bore 28 (i.e., to maintain a desired tension thereon) as will be described in more detail below. For example, the locking element may include an interference fit plug, a tube that is crushed, etc. or any other suitable device. As can be seen in FIG. 4, a proximal part of the channel 42 may include a thread 48 sized to mate with the thread 52 of a corresponding part of a set screw 50 as shown in FIGS. 9-11. A proximal end of the set screw 50 preferably includes a structure (e.g., a hex recess 51) to mate with a known tightening device (not shown) such as a screw driver, hex wrench, etc.

As shown in FIGS. 5-8, an apparatus for implanting a binding device 10 includes a mating element 54 including a first channel 56 which, when the element is in a desired position, is aligned with the bore 28 and a second channel 58 including a distal portion 60 which, when in the desired position, is aligned with the channel 42 and a proximal portion 62 which, in this embodiment, extends proximally from a proximal end of the distal portion 60 angled back toward the channel 56 to reduce a profile of the mating element 54. As would be understood by those skilled in the art, the angle between the proximal and distal portions 62, 60, respectively, should preferably be no more than 20° to avoid impeding the operation of the universal joint in a tightening tool to be inserted therethrough as will be described below. Furthermore, a maximum width of the element 54 is preferably no more than 8 mm to minimize trauma to surrounding tissue. The element 54 also includes an abutting surface 64 which, when the element 54 is in the desired position, contacts the abutment surface 18.

In use, the cable 34 is first passed around the portion(s) of fractured bone to be stabilized and the enlarged first end 36 is inserted into the groove 22 via the opening 40. The cable 34 and the enlarged first end 36 are then drawn through the groove 22 until contact between the enlarged first end 36 and the lip 38 prevents the enlarged end 36 from moving further. The second end of the cable 34 is then inserted into the distal opening 32 and passed through the bore 28 out of the proximal opening 30 and into the groove 22. The second end of the cable 34 is drawn out of the proximal opening 24 and the slack in the cable 34 is drawn out by pulling the cable 34 proximally out of the opening 24. The second end of the cable 34 is then inserted into the channel 56 and passed therethrough to a known tensioning mechanism (not shown) as the mating element 54 is moved distally over the cable 34 until the abutting surface 64 contacts the abutment surface 18. The tensioning mechanism is then operated as would be understood by those skilled in the art until a desired tension is placed on the cable 34. A tightening device including a joint (e.g., a universal joint) allowing the tightening device to navigate the bend in the channel 58 is then inserted through the channel 58 to mate with the hex recess 51. The set screw 50 is then screwed into the channel 42 until a distal end thereof extends into the bore 28 locking the cable 34 in position therein and maintaining the desired tension in the cable 34. The second end of the cable 34 may then be released from the tensioning mechanism and the portion of the cable 34 extending proximally from the groove 22 may be cut off and withdrawn from the body.

As shown in FIGS. 12-19, a binding member 100 according to a second embodiment of the invention operates in a manner substantially similar to that of the binding member 10 described above Similar to the binding member 10, the binding member 100 includes an outer surface 112, a bone facing surface 114, a distal end 116 and an abutment surface 118 formed at a proximal end 120 thereof. A groove 122 is formed in the binding member 100 extending distally from a proximal opening 124 in the abutment surface 118 to a distal end 26. However, in the binding member 100, the bore 128 does not open into the groove 122. Rather, the bore 128 extends from a proximal opening 130 in proximal end 120 to a distal opening 132 in the distal end 116. The bore 128 is preferably formed as a simple through hole sized to accept a flexible cable 34 to be held by the binding member 100. The proximal opening 124 of the groove 122 is sized so that a cable 134 may slidably pass therethrough while an enlarged first end 136 of the cable 134 is prevented from passing therethrough. The groove 122 also includes a lip 138 extending substantially around the perimeter thereof sized to permit the cable 134 to pass slidably therethrough while preventing the enlarged first end 136 from passing through. The rest of the groove 122 (i.e., an interior passage thereof) is preferably sized to permit the cable 134 and the enlarged first end 136 to slide therethrough. In addition, the groove 122 includes an enlarged distal opening 140 at a distal end 126 thereof sized to permit the enlarged first end 136 to be inserted into the groove 122. As the bore 128 does not open into the groove 122, the groove 122 does not need to be angled relative to the outer surface 112 and the bone facing surface 114. Rather, the groove 122 may extend substantially parallel to these surfaces allowing the thickness of the binding member 100 to be reduced.

The binding member 100 further comprises a locking element channel 142 extending at an angle from a proximal opening 144 to a distal opening 146 into the bore 128. As described above in regard to the binding member 10, although the channel 142 is shown as adapted to receive a set screw 50 as shown in FIGS. 9-11, any number of alternate locking elements may be employed to lock the cable 134 at a desired position in the bore 128 (i.e., to maintain a desired tension thereon). A proximal end of the set screw 50 preferably includes a structure (e.g., a hex recess 51) to mate with a known tightening device (not shown) such as a screw driver, hex wrench, etc.

As shown in FIGS. 16-19, an apparatus for implanting a binding device 100 includes a mating element 154 including a first channel (not shown) which, when the element 154 is in a desired position, is aligned with the bore 128 and a second channel (not shown) which may include an angled proximal section to reduce the profile of the element 154 similar to the distal portion 60 of the element 54 described above. The distal portion of this second channel, when in the element 154 is in the desired position, is aligned with the channel 142. The element 154 also includes an abutting surface 164 which, when the element 154 is in the desired position, contacts the abutment surface 118.

In use, the cable 134 separate from the binding member 100 is inserted around the bone to be cerclaged as would be understood by those skilled in the art and the enlarged first end 136 is inserted into the groove 122 via the opening 140. The cable 134 and the enlarged first end 136 are then drawn through the groove 122 until contact between the enlarged first end 136 and the lip 138 prevents the enlarged end 136 from moving further. The second end of the cable 134 is then inserted into the distal opening 132 and passed through the bore 128 out of the proximal opening 130. The slack in the cable 134 is drawn out by pulling the cable 134 proximally out of the opening 130 and the second end of the cable 134 is inserted into the channel 156 and passed therethrough to a known tensioning mechanism (not shown) as the mating element 154 is moved distally over the cable 134 until the abutting surface 164 contacts the abutment surface 118. The tensioning mechanism is then operated as would be understood by those skilled in the art until a desired tension is placed on the cable 134. As described above in regard to element 54, a tightening device is inserted through the second channel to mate with the hex recess 51. The set screw 50 is then screwed into the channel 142 until a distal end thereof extends into the bore 128 locking the cable 134 in position therein and maintaining the desired tension in the cable 134. The second end of the cable 134 may then be released from the tensioning mechanism and the portion of the cable 34 extending proximally from the opening 130 may be cut off and withdrawn from the body.

The present invention has been described with reference to specific exemplary embodiments. Those skilled in the art will understand that various modifications and changes may be made to the embodiments without departing from the teaching of the invention. These embodiments specification are therefore, to be regarded in an illustrative rather than a restrictive sense and are not intended to limit the scope of the invention which is intended to cover all modifications and variations of this invention that come within the scope of the appended claims and their equivalents.

What is claimed is:

1. A device for binding a cable about a fractured bone to stabilize a fracture comprising:
   a body portion having a slot extending in the body portion, the body portion having a bone facing surface, an outer surface opposite the bone facing surface and first and second side surfaces extending therebetween, the first side surface being opposite the second side surface, the slot including a distal opening sized to receive an enlarged end of the cable and a proximal opening sized smaller than the distal opening to permit the cable to slide therethrough while preventing the enlarged end from passing therethrough and a side opening, opening the slot to the outer surface between the distal opening and the proximal opening;
   a bore extending in the body portion between a distal bore opening formed in the first side surface and a proximal bore opening, opening into a distal length of the slot, the distal bore opening being axially separated from the outer surface, the bore being sized to slidably receive the cable;
   a locking element channel extending in the body portion from a proximal locking channel opening formed in the second side surface to a distal end opening into the bore; and
   a locking element movable into a locking position in the locking element channel in which a distal end of the locking element extends into the bore to engage a portion of the cable received therein and lock the cable in a desired position within the bore, the proximal opening of the slot being dimensioned so that, when both the enlarged end and a proximal length of the cable are simultaneously positioned within the slot, a second end of the cable is insertable through the slot and out of the proximal opening.

2. The device of claim 1, wherein a proximal end of the slot is offset toward a bone facing side of the of the device relative to the bore.

3. The device of claim 2, wherein the proximal end of the slot is offset toward a bone facing side of the device relative to the bore by a distance at least equal to a profile of an enlarged distal end of a cable to be used with the device.

4. The device of claim 3, wherein the slot slopes toward an outer side of the device opposite the bone facing side thereof toward a distal end of the slot.

5. The device of claim 4, wherein the slot extends substantially in a common plane with an axis of the bore.

6. The device of claim 1, wherein the bore is offset laterally from the slot.

7. The device of claim 1, wherein the locking element is a set screw.

8. The device of claim 5, wherein a proximal portion of the locking element channel includes a threading corresponding to a threading of the set screw.

9. The device of claim 1, further comprising a mating element including:
- a distal abutting surface for abutting a proximal abutting surface of the device;
- a first channel which, when in a desired position, is aligned with the bore; and
- a second channel which, when in a desired position, is aligned with the locking element channel.

10. The device of claim 9, wherein the second channel includes a proximal portion and a distal portion, the proximal portion being angled relative to the distal portion, which is angled toward the first channel.

11. The device of claim 9, wherein the mating element includes a proximal abutting surface for abutting a distal end of a tensioning device.

12. The device of claim 1, wherein the locking element comprises one of an interference fit plug and a pin in combination with a crushable section of the locking element channel, crushing of the crushable section locking the pin in a desired position within the locking element channel.

* * * * *